United States Patent
Rencher et al.

(10) Patent No.: US 10,064,675 B2
(45) Date of Patent: *Sep. 4, 2018

(54) MULTI-MODE ELECTROSURGICAL APPARATUS

(71) Applicant: Bovie Medical Corporation, Clearwater, FL (US)

(72) Inventors: Jeffrey C. Rencher, Sarasota, FL (US); Gregory A. Konesky, Hampton Bays, NY (US); Borislav S. Simeonov, St. Petersburg, FL (US); Nickolay Dimitrov Shilev, Sofia (BG); Arik Zoran, Clearwater, FL (US)

(73) Assignee: Bovie Medical Corporation, Clearwater, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/865,484

(22) Filed: Sep. 25, 2015

(65) Prior Publication Data

US 2016/0022347 A1    Jan. 28, 2016

Related U.S. Application Data

(63) Continuation of application No. 13/802,572, filed on Mar. 13, 2013, now Pat. No. 9,144,453, which is a
(Continued)

(51) Int. Cl.
*A61B 18/04* (2006.01)
*A61B 18/14* (2006.01)
(Continued)

(52) U.S. Cl.
CPC ............ *A61B 18/042* (2013.01); *A61B 18/10* (2013.01); *A61B 18/14* (2013.01);
(Continued)

(58) Field of Classification Search
CPC ....... A61B 18/042; A61B 18/10; A61B 18/14; A61B 18/1402; A61B 18/1206; A61B 18/1492
See application file for complete search history.

(56) References Cited

U.S. PATENT DOCUMENTS

| 1,813,902 A | 7/1931 | Bovie |
| 2,435,442 A | 2/1948 | Gurewitsch |
| (Continued) | | |

FOREIGN PATENT DOCUMENTS

| DE | 2429021 | 1/1976 |
| EP | 0878263 | 11/1998 |
| (Continued) | | |

OTHER PUBLICATIONS

European Search Report for European Application No. 11008861.4; dated Jan. 25, 2015; five (5) pages.
(Continued)

*Primary Examiner* — Scott Getzow
(74) *Attorney, Agent, or Firm* — Gerald E. Hespos; Michael J. Porco; Matthew T. Hespos

(57) ABSTRACT

A multi-mode electrosurgical apparatus for use in cold plasma applications, electrosurgical cutting, electrosurgical coagulation and mechanical cutting is provided. The electrosurgical apparatus includes a housing having a passage extending therethrough, an electrically conducting tube being disposed in the passage of the housing; an insulating outer tube disposed around the electrically conducting tube coupled to the housing, the electrically conducting tube being movable along a longitudinal axis of the housing and outer tube; an electrically conducting blade coupled to the distal end of the electrically conducting tube, and a transformer assembly disposed on a proximal end of the housing, the transformer assembly including a first transformer and a first switch for selectively coupling the first transformer and
(Continued)

an external second transformer to the electrically conducting tube for providing electrosurgical energy thereto.

24 Claims, 11 Drawing Sheets

Related U.S. Application Data continuation-in-part of application No. 13/289,060, filed on Nov. 4, 2011, now Pat. No. 9,060,765.

(60) Provisional application No. 61/411,174, filed on Nov. 8, 2010.

(51) Int. Cl.
  A61B 18/10 (2006.01)
  A61B 17/3209 (2006.01)
  A61B 18/00 (2006.01)
  A61B 18/12 (2006.01)
  A61B 90/00 (2016.01)

(52) U.S. Cl.
  CPC ...... *A61B 18/1402* (2013.01); *A61B 17/3209* (2013.01); *A61B 2018/00589* (2013.01); *A61B 2018/00607* (2013.01); *A61B 2018/00946* (2013.01); *A61B 2018/00958* (2013.01); *A61B 2018/00988* (2013.01); *A61B 2018/1286* (2013.01); *A61B 2018/1475* (2013.01); *A61B 2090/0811* (2016.02)

(56) References Cited

U.S. PATENT DOCUMENTS

| | | |
|---|---|---|
| 3,239,730 A | 3/1966 | Farago |
| 3,801,766 A | 4/1974 | Morrison, Jr. |
| 4,127,110 A | 11/1978 | Bullara |
| 4,196,734 A | 4/1980 | Harris |
| 4,545,375 A | 10/1985 | Cline |
| 4,580,562 A | 4/1986 | Goof et al. |
| 4,619,258 A | 10/1986 | Pool |
| 4,625,723 A | 12/1986 | Altnether et al. |
| 4,632,109 A | 12/1986 | Paterson |
| 4,708,137 A | 11/1987 | Tsukagoshi |
| 4,827,927 A | 5/1989 | Newton |
| 5,088,997 A | 2/1992 | Delahuerga et al. |
| 5,098,430 A | 3/1992 | Fleenor |
| 5,207,675 A | 5/1993 | Canady |
| 5,256,138 A | 10/1993 | Burek et al. |
| 5,269,780 A | 12/1993 | Roos |
| 5,306,238 A | 4/1994 | Fleenor |
| 5,400,267 A | 3/1995 | Denen et al. |
| 5,425,375 A | 6/1995 | Chin et al. |
| 5,445,635 A | 8/1995 | Denen et al. |
| 5,449,356 A | 9/1995 | Walbrink et al. |
| 5,626,575 A | 5/1997 | Crenner |
| 5,647,869 A | 7/1997 | Goble et al. |
| 5,651,780 A | 7/1997 | Jackson et al. |
| 5,660,657 A | 8/1997 | Rajala et al. |
| 5,693,042 A | 12/1997 | Boiarski et al. |
| 5,693,044 A | 12/1997 | Cosmescu |
| 5,776,092 A | 7/1998 | Farin et al. |
| 5,800,427 A | 9/1998 | Zamba |
| 6,063,081 A * | 5/2000 | Mulier ............ A61B 18/1402 604/35 |
| 6,193,715 B1 | 2/2001 | Wrublewski et al. |
| 6,225,593 B1 | 5/2001 | Howieson et al. |
| 6,293,945 B1 | 9/2001 | Parins et al. |
| 6,325,799 B1 | 12/2001 | Goble |
| 6,391,027 B1 | 5/2002 | Farin et al. |
| 6,409,724 B1 | 6/2002 | Penny et al. |
| 6,458,125 B1 | 10/2002 | Cosmescu |
| 6,475,215 B1 | 11/2002 | Tanrisever |
| 6,508,815 B1 | 1/2003 | Strul et al. |
| 6,558,383 B2 | 5/2003 | Cunningham et al. |
| 6,578,579 B2 | 6/2003 | Burnside et al. |
| 6,652,514 B2 | 11/2003 | Ellman et al. |
| 6,740,079 B1 * | 5/2004 | Eggers ............ A61B 18/1206 606/34 |
| 6,770,071 B2 | 8/2004 | Woloszko et al. |
| 6,899,538 B2 | 5/2005 | Matoba |
| 6,958,063 B1 | 10/2005 | Soll et al. |
| 6,994,707 B2 | 2/2006 | Ellman et al. |
| 7,033,353 B2 | 4/2006 | Stoddard et al. |
| 7,115,121 B2 | 10/2006 | Novak |
| 7,156,842 B2 | 1/2007 | Sartor et al. |
| 7,156,844 B2 | 1/2007 | Reschke et al. |
| 7,169,144 B2 | 1/2007 | Hoey et al. |
| 7,244,257 B2 | 7/2007 | Podhajsky et al. |
| 7,316,682 B2 | 1/2008 | Konesky |
| 7,335,199 B2 | 2/2008 | Goble et al. |
| 7,443,296 B2 | 10/2008 | Mezhinsky et al. |
| 7,479,140 B2 | 1/2009 | Ellman et al. |
| 7,481,809 B2 | 1/2009 | Stern et al. |
| 7,503,917 B2 | 3/2009 | Sartor et al. |
| 7,568,619 B2 | 8/2009 | Todd et al. |
| 7,578,817 B2 | 8/2009 | Canady |
| 7,654,975 B2 | 2/2010 | Mantell |
| 7,749,221 B2 | 7/2010 | Rontal |
| 7,815,638 B2 | 10/2010 | Farin et al. |
| 8,016,824 B2 | 9/2011 | Buchman, II et al. |
| 8,022,327 B2 | 9/2011 | Blomeyer |
| 8,177,782 B2 | 5/2012 | Beller et al. |
| 8,216,220 B2 | 7/2012 | Jensen et al. |
| 8,319,134 B2 | 11/2012 | Blomeyer |
| 8,353,905 B2 | 1/2013 | Jensen et al. |
| 8,562,598 B2 | 10/2013 | Falkenstein et al. |
| 8,568,400 B2 | 10/2013 | Gilbert |
| 8,689,606 B2 | 4/2014 | Schellekens et al. |
| 2002/0013582 A1 | 1/2002 | Mulier et al. |
| 2003/0050633 A1 | 3/2003 | Ellman et al. |
| 2003/0130655 A1 | 7/2003 | Woloszko et al. |
| 2004/0148903 A1 | 8/2004 | Cash |
| 2004/0243120 A1 | 12/2004 | Orszulak et al. |
| 2005/0075630 A1 | 4/2005 | Truckai et al. |
| 2005/0113820 A1 | 5/2005 | Goble et al. |
| 2005/0148903 A1 | 7/2005 | Diamantopoulos |
| 2006/0122595 A1 | 6/2006 | Farin et al. |
| 2007/0028669 A1 | 2/2007 | Brewster |
| 2007/0049926 A1 | 3/2007 | Sartor |
| 2007/0083247 A1 | 4/2007 | Wyeth et al. |
| 2007/0093810 A1 | 4/2007 | Sartor et al. |
| 2007/0135812 A1 | 6/2007 | Sartor |
| 2007/0158209 A1 | 7/2007 | Kang et al. |
| 2007/0260239 A1 | 11/2007 | Podhajsky et al. |
| 2008/0071261 A1 | 3/2008 | Orszulak |
| 2008/0108985 A1 | 5/2008 | Konesky |
| 2008/0132893 A1 | 6/2008 | D'Amelio et al. |
| 2008/0140066 A1 | 6/2008 | Davison et al. |
| 2009/0005772 A1 | 1/2009 | Penny |
| 2009/0125023 A1 | 5/2009 | Stephen et al. |
| 2009/0143778 A1 | 6/2009 | Sartor et al. |
| 2009/0149851 A1 | 6/2009 | Craig |
| 2009/0248022 A1 | 10/2009 | Falkenstein et al. |
| 2010/0094288 A1 * | 4/2010 | Kerr ............ A61B 18/1206 606/51 |
| 2010/0262139 A1 | 10/2010 | Beller et al. |
| 2011/0238053 A1 | 9/2011 | Brannan et al. |
| 2011/0276113 A1 | 11/2011 | Cybulski |
| 2012/0116397 A1 | 5/2012 | Rencher et al. |
| 2012/0123405 A1 | 5/2012 | Moua et al. |
| 2012/0232540 A1 | 9/2012 | Baur et al. |
| 2012/0330305 A1 | 12/2012 | Zoran et al. |
| 2012/0330307 A1 | 12/2012 | Ladtkow et al. |
| 2013/0046290 A1 | 2/2013 | Palmer et al. |
| 2013/0237982 A1 | 9/2013 | Rencher et al. |
| 2013/0296846 A1 | 11/2013 | Canady et al. |

(56) References Cited

U.S. PATENT DOCUMENTS

2014/0005665 A1    1/2014    Konesky et al.
2014/0018795 A1    1/2014    Shilev et al.

FOREIGN PATENT DOCUMENTS

| EP | 0186369    | 3/2003  |
|----|------------|---------|
| EP | 1764057    | 3/2007  |
| EP | 2263728    | 12/2010 |
| EP | 2449992    | 5/2012  |
| WO | WO03082134 | 10/2003 |
| WO | 2004096315 | 11/2004 |

OTHER PUBLICATIONS

European Search Report for European Application No. 15000707.8; dated May 28, 2015; four (4) pages.
European Search Report for European Application No. 13003717.9; dated Sep. 17, 2014; six (6) pages.
European Search Report for European Application No. 13005083.4; dated Sep. 23, 2014; six (6) pages.
European Search Report for European Application No. 18000289.1; dated Jun. 26, 2018; eight (8) pages.

* cited by examiner

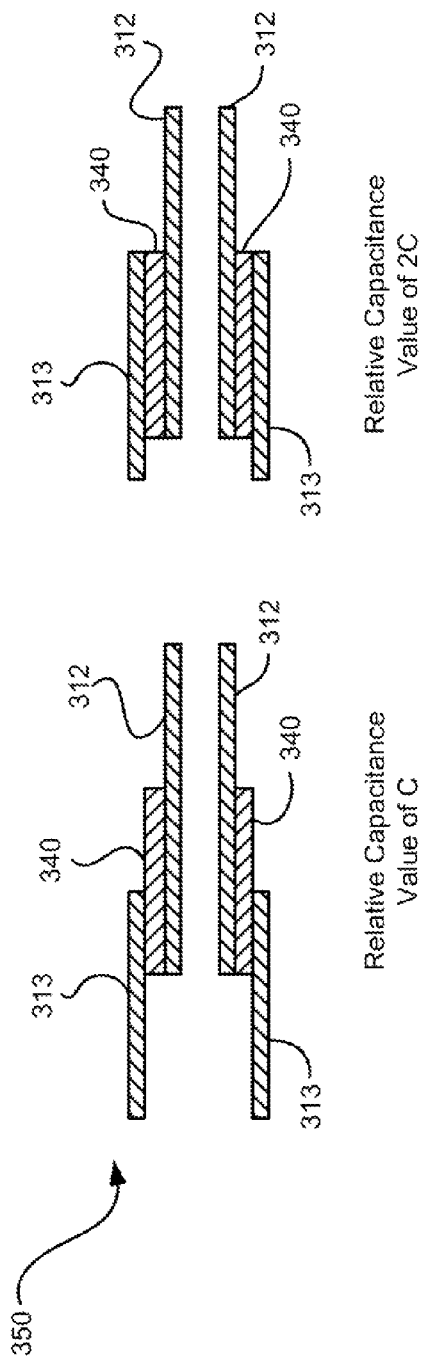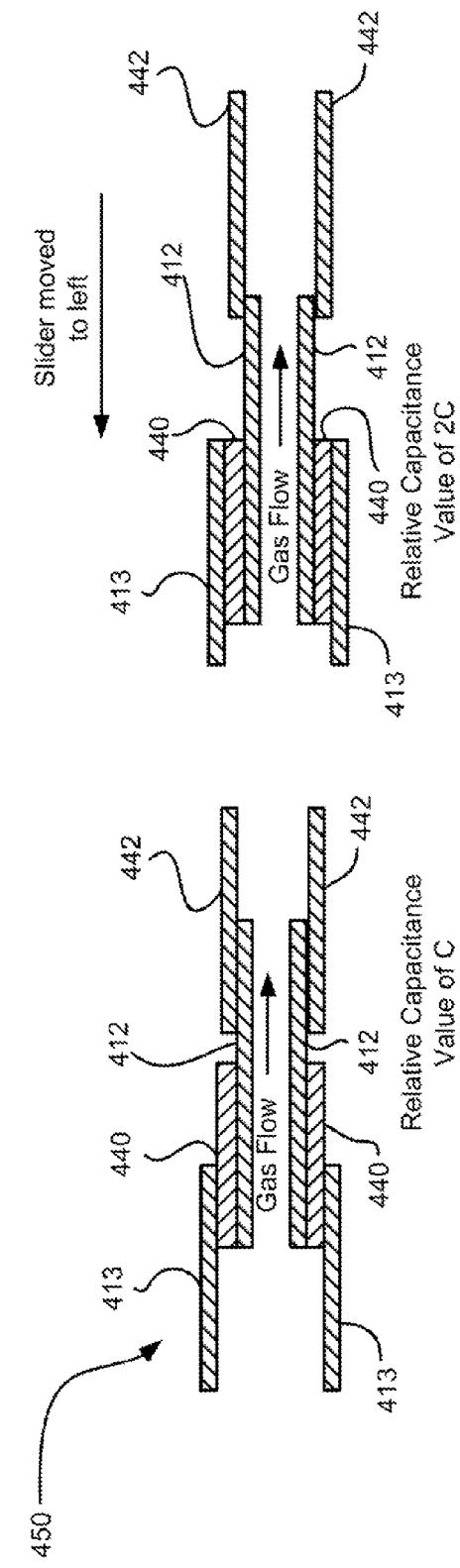

MULTI-MODE ELECTROSURGICAL APPARATUS

PRIORITY

This application is a continuation application of U.S. application Ser. No. 13/802,572, filed Mar. 13, 2013, now U.S. Pat. No. 9,144,453, which is a continuation-in-part application of U.S. application Ser. No. 13/289,060 filed Nov. 4, 2011, now U.S. Pat. No. 9,060,765, which claims priority on U.S. Provisional Patent Appl. No. 61/411,174, filed Nov. 8, 2010, entitled "ELECTROSURGICAL APPARATUS WITH RETRACTABLE BLADE", the content of both of which are hereby incorporated by reference in their entireties.

BACKGROUND

Field

The present disclosure relates generally to electrosurgery and electrosurgical systems and apparatuses, and more particularly, to an electrosurgical apparatus with a retractable blade for use in cold plasma applications, electrosurgical cutting and mechanical cutting.

Description of the Related Art

High frequency electrical energy has been widely used in surgery. Tissue is cut and bodily fluids are coagulated using electrosurgical energy.

Electrosurgical instruments generally comprise "monopolar" devices or "bipolar" devices. Monopolar devices comprise an active electrode on the electrosurgical instrument with a return electrode attached to the patient. In monopolar electrosurgery, the electrosurgical energy flows through the active electrode on the instrument through the patient's body to the return electrode. Such monopolar devices are effective in surgical procedures where cutting and coagulation of tissue are required and where stray electrical currents do not pose a substantial risk to the patient.

Bipolar devices comprise an active electrode and a return electrode on the surgical instrument. In a bipolar electrosurgical device, electrosurgical energy flows through the active electrode to the tissue of a patient through a short distance through the tissue to the return electrode. The electrosurgical effects are substantially localized to a small area of tissue that is disposed between the two electrodes on the surgical instrument. Bipolar electrosurgical devices have been found to be useful with surgical procedures where stray electrical currents may pose a hazard to the patient or where other procedural concerns require close proximity of the active and return electrodes. Surgical operations involving bipolar electrosurgery often require methods and procedures that differ substantially from the methods and procedures involving monopolar electrosurgery.

Gas plasma is an ionized gas capable of conducting electrical energy. Plasmas are used in surgical devices to conduct electrosurgical energy to a patient. The plasma conducts the energy by providing a pathway of relatively low electrical resistance. The electrosurgical energy will follow through the plasma to cut, coagulate, desiccate, or fulgurate blood or tissue of the patient. There is no physical contact required between an electrode and the tissue treated.

Electrosurgical systems that do not incorporate a source of regulated gas can ionize the ambient air between the active electrode and the patient. The plasma that is thereby created will conduct the electrosurgical energy to the patient, although the plasma arc will typically appear more spatially dispersed compared with systems that have a regulated flow of ionizable gas.

Atmospheric pressure discharge cold plasma applicators have found use in a variety of applications including surface sterilization, hemostasis, and ablation of tumors. In the latter example, the process can be relatively slow, generate large volumes of noxious smoke with vaporized and charred tissue, and may cause collateral damage to surrounding healthy tissue when high power electrosurgical energy is used. Precision accuracy can also be a problem, due to the width of the plasma beam.

Often, a simple surgical knife is used to excise the tissue in question, followed by the use of a cold plasma applicator for cauterization, sterilization, and hemostasis. An improved approach would have both facilities in the same surgical tool.

SUMMARY

The present disclosure relates to an electrosurgical apparatus with a retractable blade for use in cold plasma applications, electrosurgical cutting, electrosurgical coagulation and mechanical cutting. When the blade is retracted within the electrosurgical apparatus, it is electrically energized while an inert gas flows over it, producing a cold plasma discharge. In the de-energized state, the blade is advanced and used as a traditional surgical blade making contact with tissue to achieve mechanical cutting. Additionally, the blade may be advanced and used while both electrically energized and with inert gas flow. In this mode, the apparatus may be employed for electrosurgical cutting or coagulation.

In one aspect of the present disclosure, an electrosurgical apparatus includes a housing having a passage extending therethrough, the housing having a proximal end and a distal end; an electrically conducting tube having a proximal end and a distal end, the electrically conducting tube being disposed in the passage of the housing; an insulating outer tube having a proximal end and a distal end, the outer tube disposed around the electrically conducting tube with the proximal end of the outer tube coupled to the distal end of the housing, the electrically conducting tube being movable along a longitudinal axis of the housing and outer tube; an electrically conducting blade coupled to the distal end of the electrically conducting tube, and a transformer assembly disposed on the proximal end of the housing, the transformer assembly including a first transformer and a first switch for selectively coupling the first transformer and an external second transformer to the electrically conducting tube for providing electrosurgical energy thereto.

In another aspect, the electrosurgical apparatus further includes a first slider member coupled to the electrically conducting tube for moving the electrically conducting tube thereby extending and retracting the blade about the distal end of the outer tube, the first slider member being accessible on the housing.

In a further aspect, the electrosurgical apparatus includes a second slider member coupled to the switch and configured to operate the switch, the second slider member being accessible on the housing.

In another aspect, the first transformer is a step-up transformer and is configured to receive electrosurgical energy at a first predetermined value and the external second transformer is configured to provide electrosurgical energy to the electrically conducting tube at a second predetermined value.

In yet another aspect, the electrosurgical apparatus includes a plurality of buttons configured to affect at least one electrosurgical mode based on a position of the first switch.

In another aspect, the electrosurgical apparatus includes a second switch configured to determine a position of the blade and generate a signal indicating the position, the signal being transmitted to an electrosurgical generator.

In a further aspect, the proximal end of the electrically conducting tube includes a connector for coupling to a gas source to enable gas to flow through the electrically conducting tube over the blade.

According to another aspect of the present disclosure, an electrosurgical apparatus is provided including an electrosurgical generator coupled to an electrical power supply configured to generate electrosurgical energy, the electrosurgical generator including a step-down transformer coupled to the electrical power source and a first step-up transformer coupled to an output of the step-down transformer; and a handpiece including: a housing having a passage extending therethrough, the housing having a proximal end and a distal end; an electrically conducting tube having a proximal end and a distal end, the electrically conducting tube being disposed in the passage of the housing; an insulating outer tube having a proximal end and a distal end, the outer tube disposed around the electrically conducting tube with the proximal end of the outer tube coupled to the distal end of the housing, the electrically conducting tube being movable along a longitudinal axis of the housing and outer tube; an electrically conducting blade coupled to the distal end of the electrically conducting tube, and a transformer assembly disposed on the proximal end of the housing, the transformer assembly including a second step-up transformer and a first switch for selectively coupling the first step-up transformer and the second step-up transformer to the electrically conducting tube for providing electrosurgical energy thereto.

BRIEF DESCRIPTION OF THE DRAWINGS

The above and other aspects, features, and advantages of the present disclosure will become more apparent in light of the following detailed description when taken in conjunction with the accompanying drawings in which:

FIGS. 6A and 6B illustrate a variable structural capacitor to be employed in an electrosurgical apparatus in accordance with an embodiment of the present disclosure;

FIGS. 7A and 7B illustrate a variable structural capacitor to be employed in an electrosurgical apparatus in accordance with another embodiment of the present disclosure;

Figure 1:
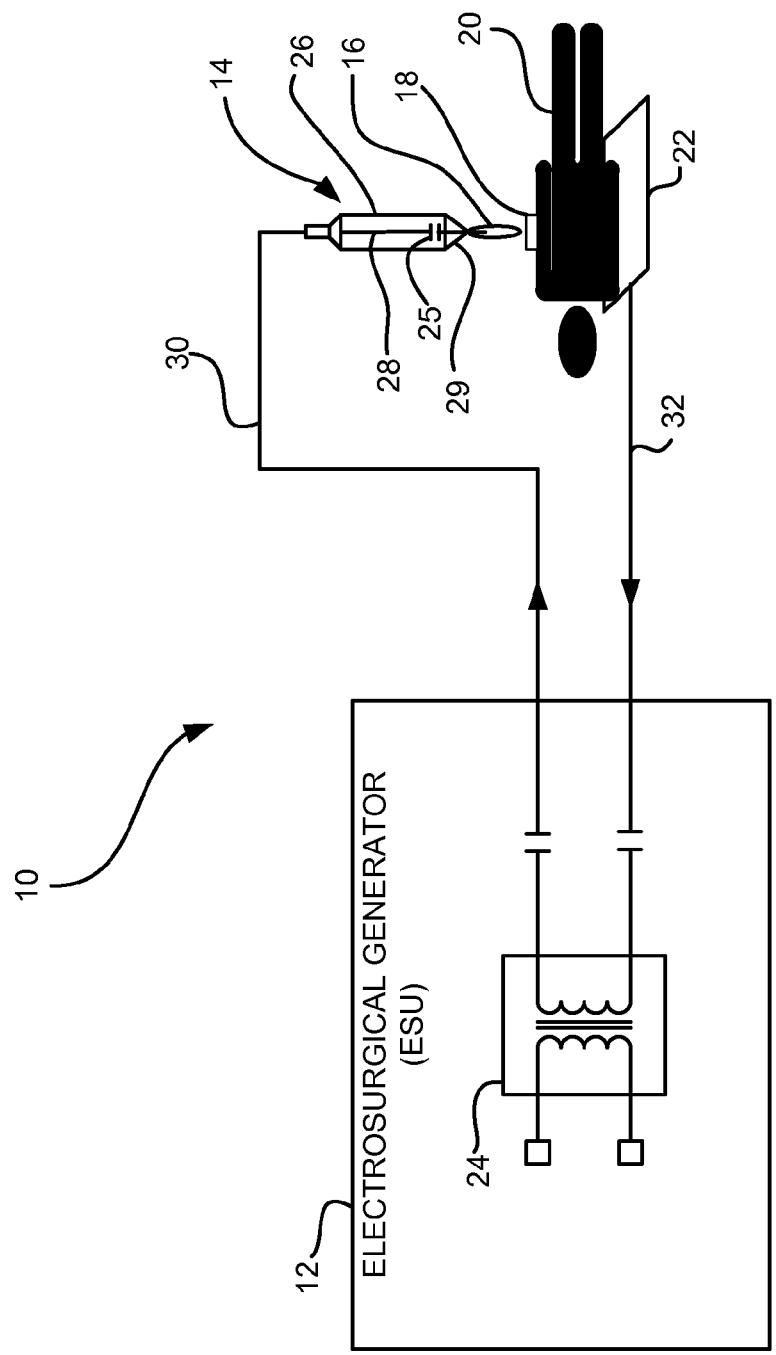
FIG. 1 is an illustration of an exemplary monopolar electrosurgical system in accordance with an embodiment of the present disclosure.

It should be understood that the drawing(s) is for purposes of illustrating the concepts of the disclosure and is not necessarily the only possible configuration for illustrating the disclosure.

DETAILED DESCRIPTION

Preferred embodiments of the present disclosure will be described hereinbelow with reference to the accompanying drawings. In the following description, well-known functions or constructions are not described in detail to avoid obscuring the present disclosure in unnecessary detail. In the drawings and in the description which follow, the term "proximal", as is traditional, will refer to the end of the device, e.g., instrument, apparatus, applicator, handpiece, forceps, etc., which is closer to the user, while the term "distal" will refer to the end which is further from the user. Herein, the phrase "coupled" is defined to mean directly connected to or indirectly connected with through one or more intermediate components. Such intermediate components may include both hardware and software based components.

FIG. 1 shows an exemplary monopolar electrosurgical system generally indicated as 10 comprising an electrosurgical generator (ESU) generally indicated as 12 to generate power for the electrosurgical apparatus 10 and a plasma generator generally indicated as 14 to generate and apply a plasma stream 16 to a surgical site or target area 18 on a patient 20 resting on a conductive plate or support surface 22. The electrosurgical generator 12 includes a transformer generally indicated as 24 including a primary and secondary coupled to an electrical source (not shown) to provide high frequency electrical energy to the plasma generator 14. Typically, the electrosurgical generator 12 comprises an isolated floating potential not referenced to any potential. Thus, current flows between the active and return electrodes. If the output is not isolated, but referenced to "earth", current can flow to areas with ground potential. If the contact surface of these areas and the patient is relatively small, an undesirable burning can occur.

The plasma generator 14 comprises a handpiece or holder 26 having an electrode 28 at least partially disposed within a fluid flow housing 29 and coupled to the transformer 24 to receive the high frequency electrical energy therefrom to at least partially ionize noble gas fed to the fluid flow housing 29 of the handpiece or holder 26 to generate or create the plasma stream 16. The high frequency electrical energy is fed from the secondary of the transformer 24 through an active conductor 30 to the electrode 28 (collectively active electrode) in the handpiece 26 to create the plasma stream 16 for application to the surgical site 18 on the patient 20.

Furthermore, a current limiting capacitor 25 is provided in series with the electrode 28 to limit the amount of current being delivery to the patient 20.

The return path to the electrosurgical generator 12 is through the tissue and body fluid of the patient 20, the conductor plate or support member 22 and a return conductor 32 (collectively return electrode) to the secondary of the transformer 24 to complete the isolated, floating potential circuit.

In another embodiment, the electrosurgical generator 12 comprises an isolated non-floating potential not referenced to any potential. The plasma current flow back to the electrosurgical generator 12 is through the tissue and body fluid and the patient 20. From there, the return current circuit is completed through the combined external capacitance to the plasma generator handpiece 26, surgeon and through displacement current. The capacitance is determined, among other things, by the physical size of the patient 20. Such an electrosurgical apparatus and generator are described in commonly owned U.S. Pat. No. 7,316,682 to Konesky, the contents of which are hereby incorporated by reference in its entirety.

It is to be appreciated that transformer 24 may be disposed in the plasma generator handpiece 26, as will be described in various embodiments below. In this configuration, other transformers may be provided in the generator 12 for providing a proper voltage and current to the transformer in the handpiece, e.g., a step-down transformer, a step-up transformer or any combination thereof.

Figure 2A:
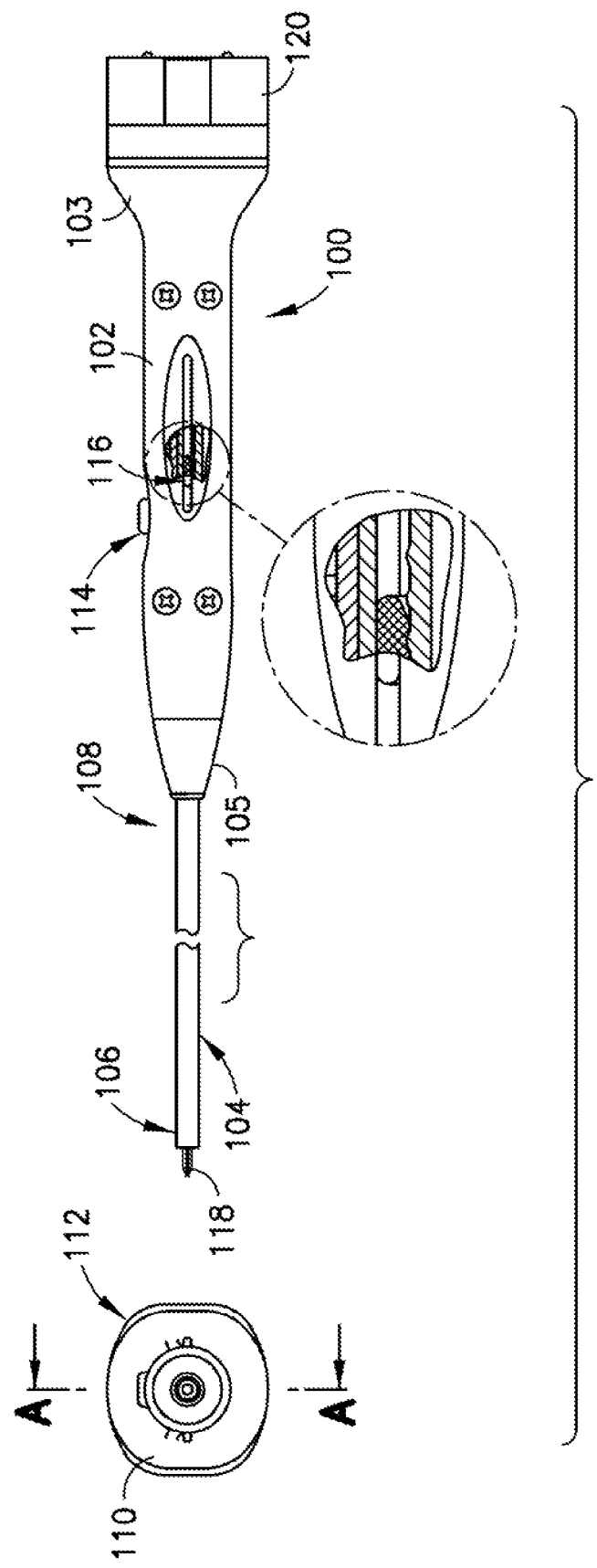
FIG. 2A is a schematic diagram of an electrosurgical apparatus in accordance with an embodiment of the present disclosure.

Referring to FIG. 2A, an electrosurgical apparatus 100 in accordance with the present disclosure is illustrated. Generally, the apparatus 100 includes a housing 102 having a proximal end 103 and a distal end 105 and a tube 104 having an open distal end 106 and a proximal end 108 coupled to the distal end 105 of the housing 102. The housing 102 includes a right side housing 110 and left side housing 112, and further includes provisions for a button 114 and slider 116. Activation of the slider 116 will expose a blade 118 at the open distal end 106 of the tube 104. Activation of the button 114 will apply electrosurgical energy to the blade 118 and, in certain embodiments, enable gas flow through the flow tube 122, as will be described in detail below.

Additionally, a transformer 120 is provided on the proximal end 103 of the housing for coupling a source of radio frequency (RF) energy to the apparatus 100. By providing the transformer 120 in the apparatus 100 (as opposed to locating the transformer in the electrosurgical generator), power for the apparatus 100 develops from higher voltage and lower current than that required when the transformer is located remotely in the generator, which results in lower thermalization effects. In contrast, a transformer back in the generator produces applicator power at a lower voltage, higher current with greater thermalization effects. Therefore, by providing the transformer 120 in apparatus 100, collateral damage to tissue at the operative site is minimized.

Figure 2B:
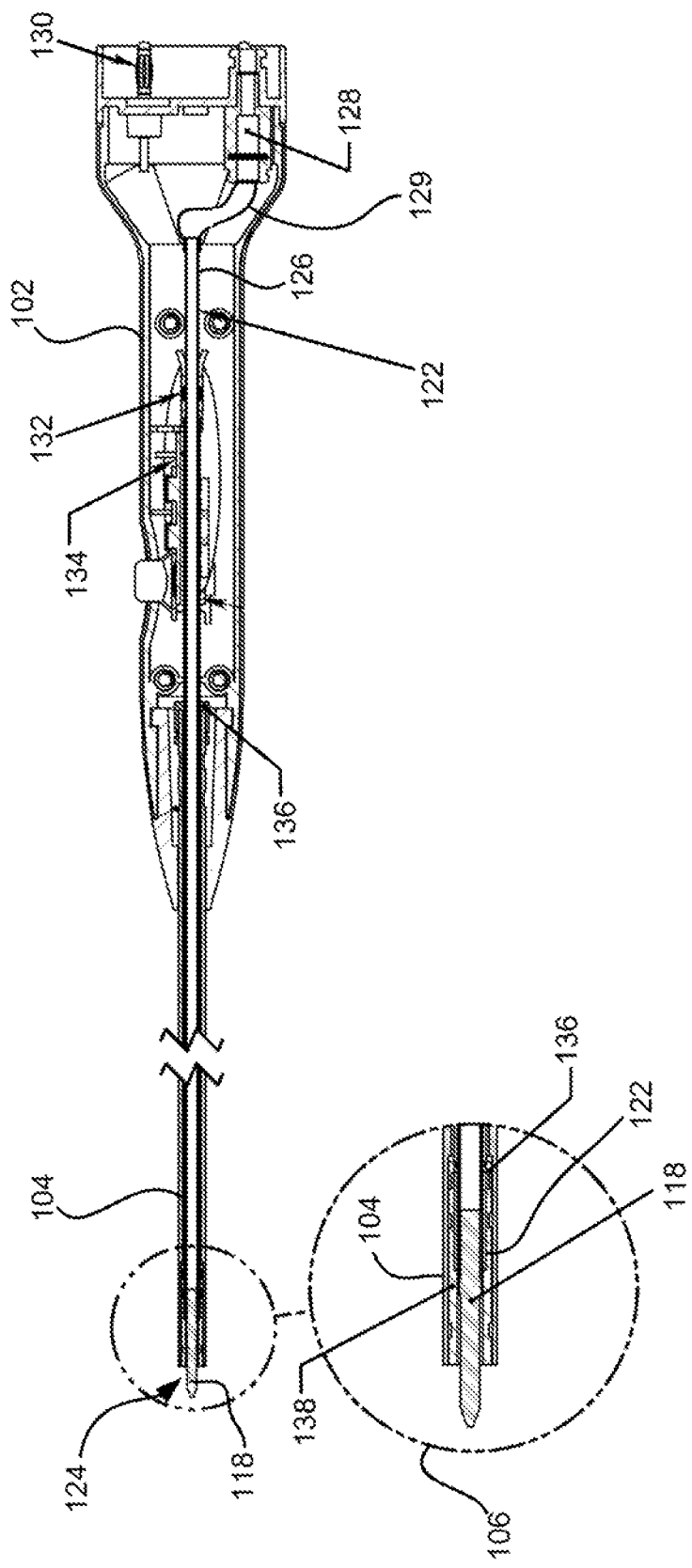
FIG. 2B is a cross sectional view of the electrosurgical apparatus shown in FIG. 2A taken along line A-A.

A cross section view along line A-A of the apparatus 102 is shown in FIG. 2B. Disposed within the housing 102 and tube 104 is flow tube 122 which runs along the longitudinal axis of the apparatus 100. On a distal end 124 of the flow tube 122, the blade 118 is retained within the flow tube 122. A proximal end 126 of the flow tube 122 is coupled to a source of gas via a tube connector 128 and flexible tubing 129. The proximal end 126 of the flow tube 122 is also coupled to a source of RF energy via plug 130 which couples to transformer 120. The flow tube 122 is made of an electrically conducting material, preferably stainless steel, as to conduct the RF energy to the blade 118 when being employed for plasma applications or electrosurgical cutting as will be described below. The outer tube 104 is constructed from non-conductive material, e.g., Lestran. The slider 116 is coupled to the flow tube 122 via a retaining collar 132. A printed circuit board (PCB) 134 is disposed in the housing 102 and controls the application of the RF energy from the transformer 120 via the button 114.

It is to be appreciated that the slider 116 may be freely moveable in a linear direction or may include a mechanism for incremental movements, e.g., a ratchet movement, to prevent an operator of the apparatus 100 from over extending the blade 118. By employing a mechanism for incremental movements of the blade 118, the operator will have greater control over the length of the exposed blade 118 to avoid damage to tissue at the surgical site.

An enlarged view of the distal end 106 of the outer tube 104 is also illustrated in FIG. 2B. Here, the blade 118 is coupled to the flow tube 122 which is held in place in the outer tube 104 by at least one seal 136. The at least one seal 136 prevents backflow of gas into tube 104 and housing 102. A cylindrical ceramic insert 138 is disposed in the distal end of the outer tube 104 to maintain the blade along the longitudinal axis of the apparatus 100 and provide structural support during mechanical cutting when the blade is exposed beyond the distal end of the outer tube 104.

Figure 3A:
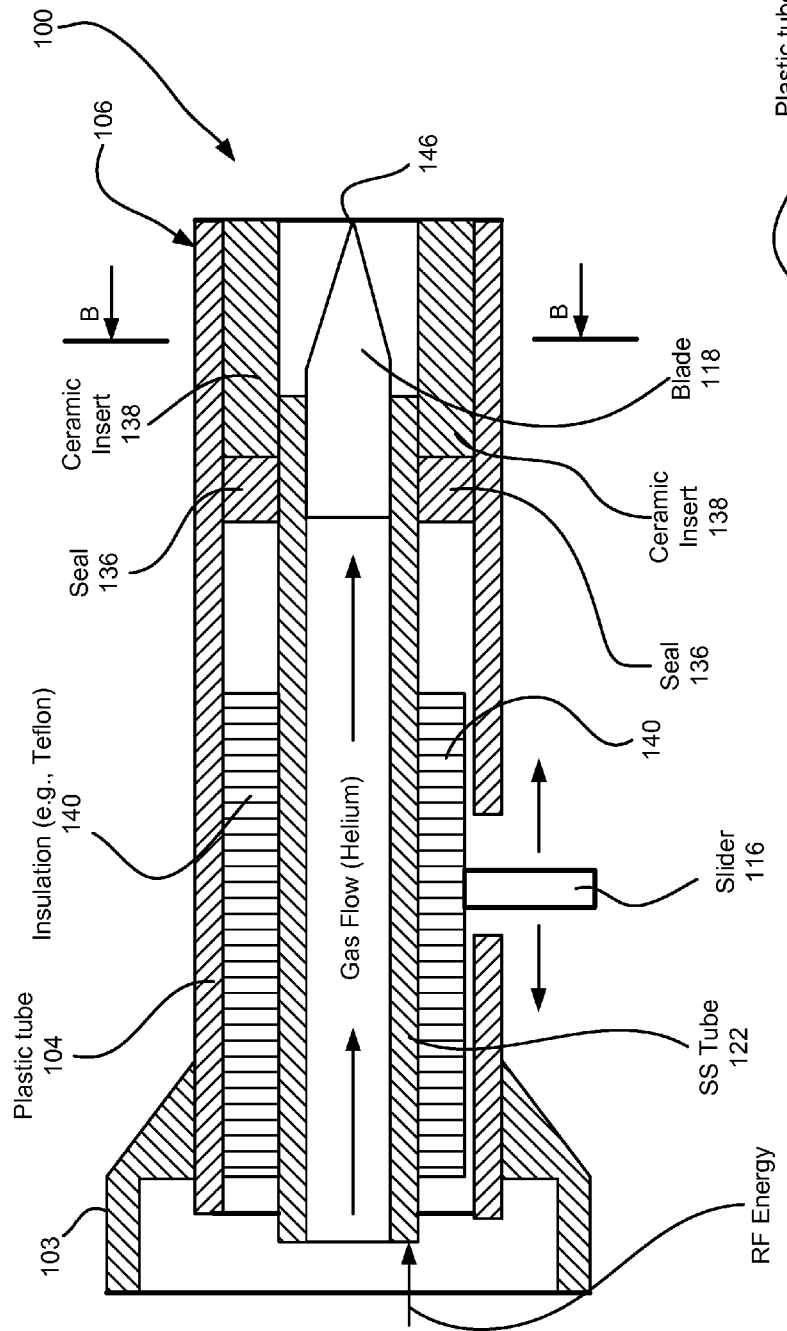
FIG. 3A is an enlarged cross sectional view of the electrosurgical apparatus in accordance with an embodiment of the present disclosure.
Figure 3B:
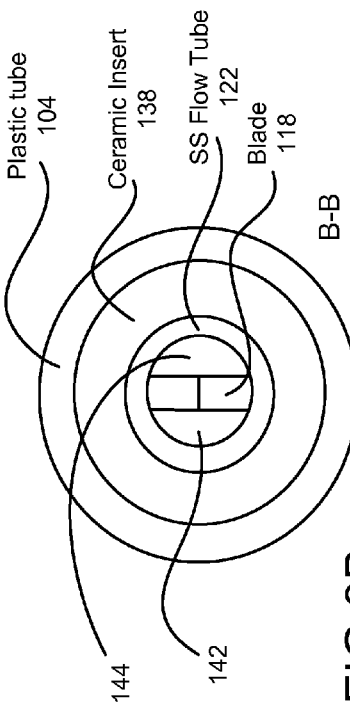
FIG. 3B illustrates a front view of the electrosurgical apparatus shown in FIG. 3A taken along line B-B.

The operational aspect of the apparatus 100 will now be described in relation to FIGS. 3A and 3B, where FIG. 3A shows an enlarged cross section of the apparatus and FIG. 3B illustrates a front view of the apparatus.

Referring to FIG. 3A, the flow tube 122 is disposed in the outer tube 104 with a cylindrical insulator 140 disposed around the flow tube 122. Slider 116 is coupled to the insulator 140 and is employed to extend and retract the blade 118. At the distal end 106 of the outer tube 104, the annular or ring shaped seal 136 and cylindrical ceramic insert 138 are disposed about the flow tube 122. As can be seen In FIG. 3B, the generally planar blade 118 is coupled to an inner circumference of the cylindrical flow tube 122 such that two gas passageways 142, 144 are formed on both sides of the blade 118. As gas flows from the proximal end 103 of the housing through the flow tube 122, the gas will pass over the blade 118 out the distal end 106 of the outer tube 104.

When the blade is in the retracted position as shown in FIG. 3A, the apparatus 100 is suitable for generating plasma. In the retracted position, RF energy is conducted to a tip 146 of the blade 118 from an electrosurgical generator (not shown) via the flow tube 122. An inert gas, such as helium or argon, is then supplied to the flow tube from either the electrosurgical generator or an external gas source. As the inert gas flows over the sharp point 146 of the blade 118 that is held at a high voltage and high frequency, a cold plasma beam is generated.

Figure 4:
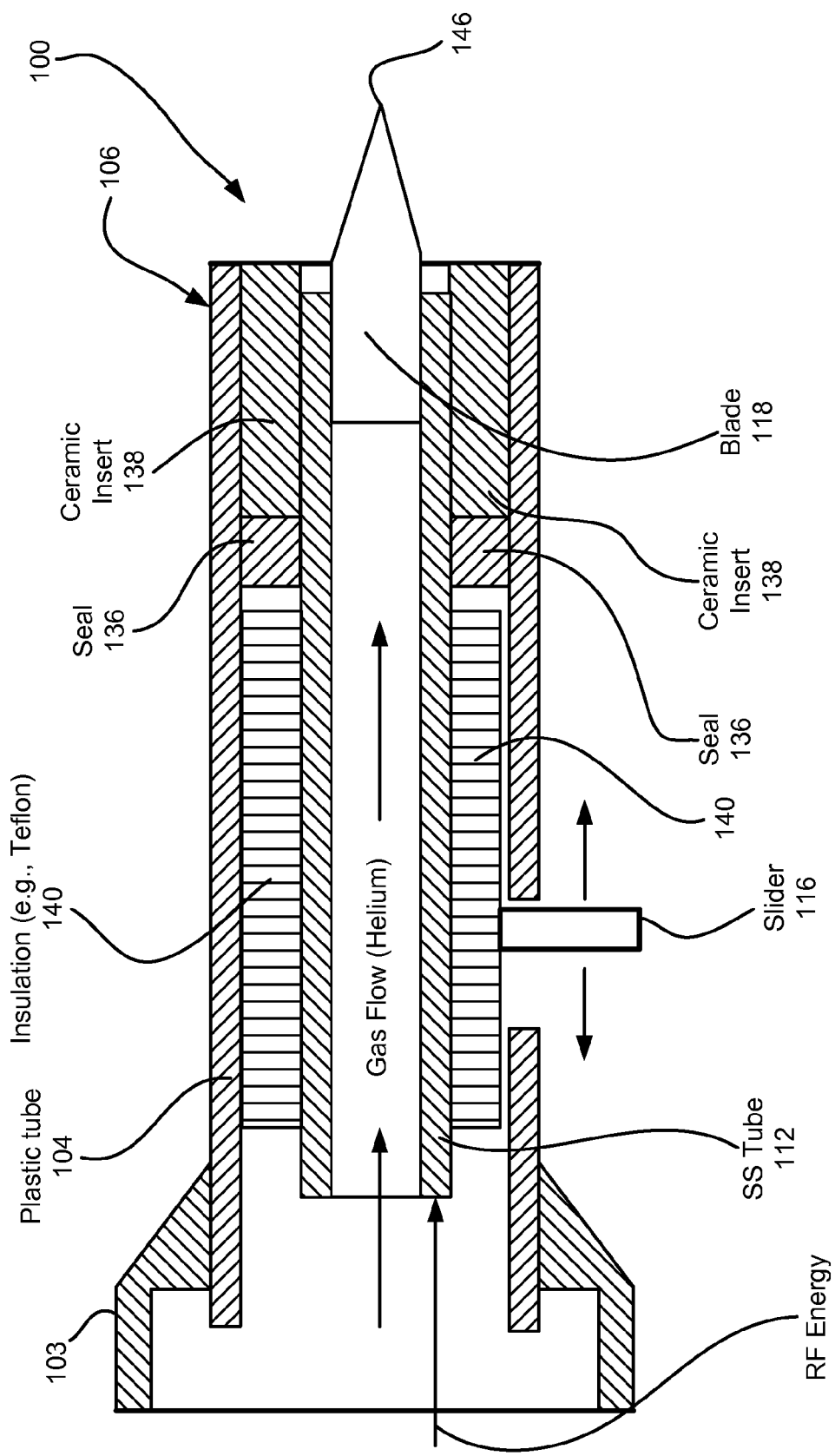
FIG. 4 is an enlarged cross sectional view of the electrosurgical apparatus shown in FIG. 3A with a blade extended.

Referring to FIG. 4, the blade 118 is advanced, via slider 116, so the tip 146 is extended pass the distal end 106 of the outer tube 104. In this state, the blade 118 can be used for two cutting modes: mechanical cutting and electrosurgical cutting. In the mechanical cutting mode, RF or electrosurgical energy is not applied to the flow tube 122 or blade 118, and therefore, the blade 118 is in a de-energized state. In this mode, the blade 118 can be used to excise tissue via mechanical cutting. After the tissue is removed, the blade 118 may be retracted via the slider 116 and electrosurgical energy and gas may be applied via button 114 to generate a cold plasma beam for cauterization, sterilization and/or hemostasis of the operative patient site.

In the electrosurgical cutting mode, the blade 118 is advanced and used while both electrically energized and with inert gas flow. This configuration resembles an electrosurgical knife approach, where the electrosurgical energy does the cutting. However, with the addition of the inert gas flow, cuts made show virtually no eschar, with very little collateral damage along the side walls of the cut. The cutting speed is considerably faster, with less mechanical cutting resistance as compared to when the knife blade is not electrically energized, i.e., the mechanical cutting mode. Hemostasis is also affected during this process.

Figure 5:
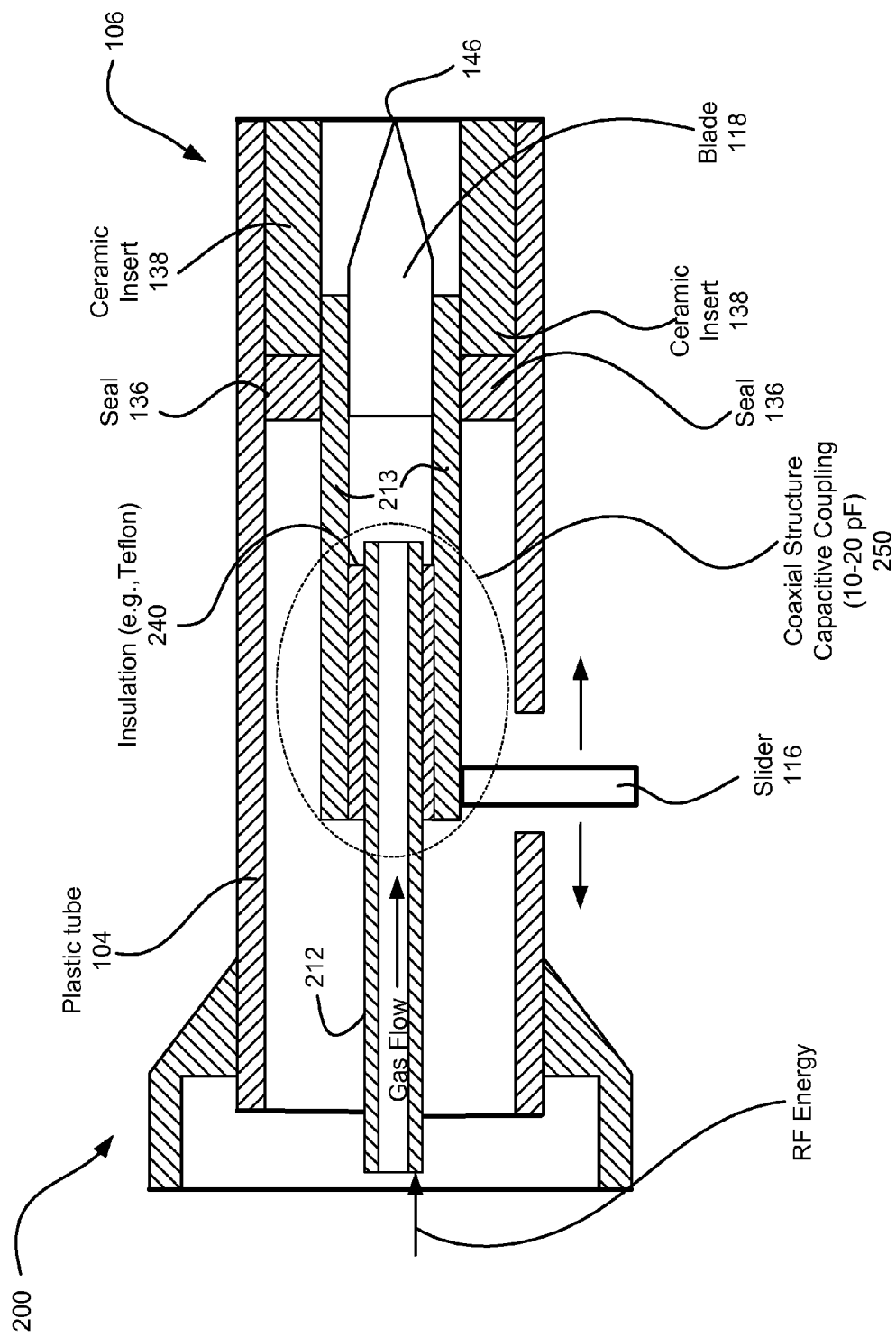
FIG. 5 is a cross sectional view of an electrosurgical apparatus in accordance with another embodiment of the present disclosure.

In another embodiment, an electrosurgical apparatus 200 as shown in FIG. 5 is configured with a structural current limiting capacitor in the distal end of the apparatus or handpiece to limit the current applied to the operative site of the patient. Generally, a capacitor is formed by two parallel conductive plates with an insulating dielectric material in between them. The capacitance is defined by:

$$C = K \in_0 (A/d) \quad (1)$$

where C is the capacitance in Farads, K is the dielectric constant (sometimes called "relative permittivity"), $\in_0$ is the permittivity of free space (approximately $8.854 \times 10^{-12}$ Farad/meter), A is the area of the capacitor plates, and d is their separation distance. Some typical values for dielectric constant are 1.000 for a vacuum (by definition), 1.00054 for air, 3.8 for fused quartz, and 2.1 for polytetrafluoroethylene ("Teflon"). The parallel plates of a capacitor can take the form of concentric conductive tubes with the insulating dielectric between them as shown In FIG. 5, and can also form a structural, as well as electrical element.

Referring to the embodiment shown in FIG. 5, the flow tube of the apparatus 200 includes a first inner flow tube 212 coupled to a second, outer flow tube 213. The inner flow tube 212 has a smaller outer diameter than the inner diameter of the outer flow tube 213. A cylindrical insulator 240 is disposed around a distal portion of the inner flow tube 212 and then inserted into the outer flow tube 213. As shown in FIG. 5, the inner flow tube 212 is inserted into the outer flow tube 213 approximately a distance equal to the length of the insulator 240. The resulting coaxial structure 250 creates a capacitive coupling for the inner and outer flow tubes 212, 213, where the total capacitance is approximately equal to the capacitance of the coaxial structure 250 plus the capacitance of the remaining length of outer flow tube 213. The coaxial structure 250 acts as a current-limiting capacitor limiting the current applied to the operative site of the patient. When the slider 116 is moved to either extend or retract the blade 118, the components of the coaxial structure 250, including the inner flow tube 212, insulator 240 and outer flow tube 213, move together as a fixed unit. In other aspects, the operation of the embodiment shown in FIG. 5 is similar to the embodiments described above.

In a further embodiment, the electrosurgical apparatus of the present disclosure will include a variable structural capacitor 350 as shown in FIGS. 6A and 6B. The capacitance of a structural capacitor can be varied, assuming a fixed dielectric constant K, by varying the area between the inner and outer conductive tubes. Referring to FIGS. 6A and 6B, inner conductive tube 312 and outer conductive tube 313 are configured to slide relative to each other, with a sleeve of dielectric insulator 340 between them fixed to one of the inner or outer tubes 312, 313 respectively. The degree of overlap of the inner and outer conductive tubes 312, 313 affects the resulting capacitance. In the example shown in FIG. 6A, the insulating dielectric sleeve 340 is fixed to the inner conductive tube 312. The approximately 50% overlap of the outer tube 313 over insulator 340, shown in FIG. 6A, results in a relative capacitance value of "C" and 100% overlap shown in FIG. 6B, in a capacitance of "2C."

While capacitors will block direct current, and provide protection from galvanic currents in an electrosurgical application, capacitors will pass alternating currents as a result of their capacitive reactance, which is defined by:

$$X_C = 1/(2 \pi f C) \quad (2)$$

where $X_C$ is the capacitive reactance (in units of resistance), C is the capacitance, and f is the frequency. Due to this inverse relationship, as the capacitance increases, the capacitive reactance decreases. For a given applied voltage and fixed frequency, as the capacitance increases, the amount of current limited by this capacitor will also increase as a result of decreased capacitive reactance.

In the example shown in FIGS. 6A and 6B, the capacitance setting in FIG. 6A limits the current to a lower value than the setting shown in FIG. 6B. In this embodiment, a second slider (not shown) provides the opportunity to adjust this value at the hand piece during a surgical procedure, without being interrupted to make an adjustment at the generator.

It is important to note that when adjusting the current limiting value through varying the relative positions of the inner and outer conductive tubes, that other moveable components, such as the position of the retractable blade, not also be affected. One way to achieve this is with a dual slider configuration 450 as shown in FIGS. 7A and 7B. One side of the slider, or inner conductive tube 412, has the dielectric insulating sleeve 440 to act as the adjustable current limiting capacitor. The other side simply maintains electrical contact to a second outer conductive tube 442 which attaches to the retractable blade (not shown), and allows relative movement without disturbing the position of the retractable blade. This is illustrated in FIGS. 7A and 7B, showing a low current limit value on the left (FIG. 7A), and a high current limit value on the right (FIG. 7B). The position of the inner "slider" tube 412 may be controlled manually by the surgeon via a first slider member, or automatically by electromechanical, pneumatic or similar means. This provides the opportunity to create a feedback loop where the current limit is self-adjusted based on a measured parameter such as absorbed power, tissue temperature, tissue impedance or tissue type. A second slider member may be provided and coupled to the outer tube 442 to extend and retract the blade, when the blade is coupled to the distal end of the outer tube 442.

Figure 8:
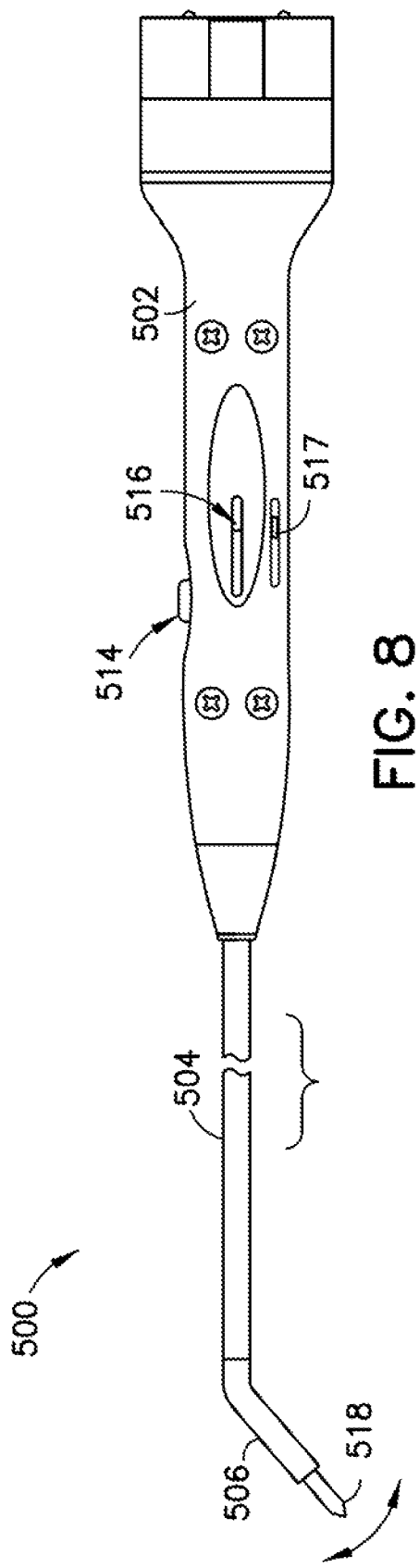
FIG. 8 illustrates an exemplary electrosurgical apparatus including an articulating distal end in accordance with an embodiment of the present disclosure.

In a further embodiment, the electrosurgical apparatus of the present disclosure will have an articulating distal end. Referring to FIG. 8, the electrosurgical apparatus 500 will have similar aspects to the embodiments described above with the distal end 506, e.g., approximately 2 inches, being flexible to maneuver the distal end 506 at the surgical site. An additional control 517, e.g., a slider, trigger, or the like, is provided in the proximal housing 502 to control the bending of the distal end 506. As in the above described embodiments, a button 514 is provided to apply electrosurgical energy to the blade 518 and, in certain embodiment, enable gas flow through the flow tube. Furthermore, slider 516 will expose the blade 518 at the open distal end 506 upon activation.

In one embodiment, the articulating control 517 will include two wires, one pulling to articulate and one pulling to straighten the distal end 506. The outer tube 504 will be the similar to the design shown in FIG. 2 and will be rigid, preferably made of Ultem™ or similar material, up to the last 2 inches which would be made of a material similar to that of a gastrointestinal (GI) flexible scope. In certain embodiments, inside the outer tube 504 is constructed of a mesh infused Teflon™ or similar material and a flexible insulating material that would allow the distal end 506 to bend at least 45° and not collapse the inner tube carrying the gas. The blade 518 will be made of a flexible metallic material such as Nitinol™ that would be able to bend but would retain it's memory in the straightened position. Alternatively, a straight metal blade 518 would be provided with the distal 2 inches made of a linked metal such that it would still carry a current but would be bendable and the cutting portion of the blade 518 would be attached to the distal end of the linked portion.

Figure 9:
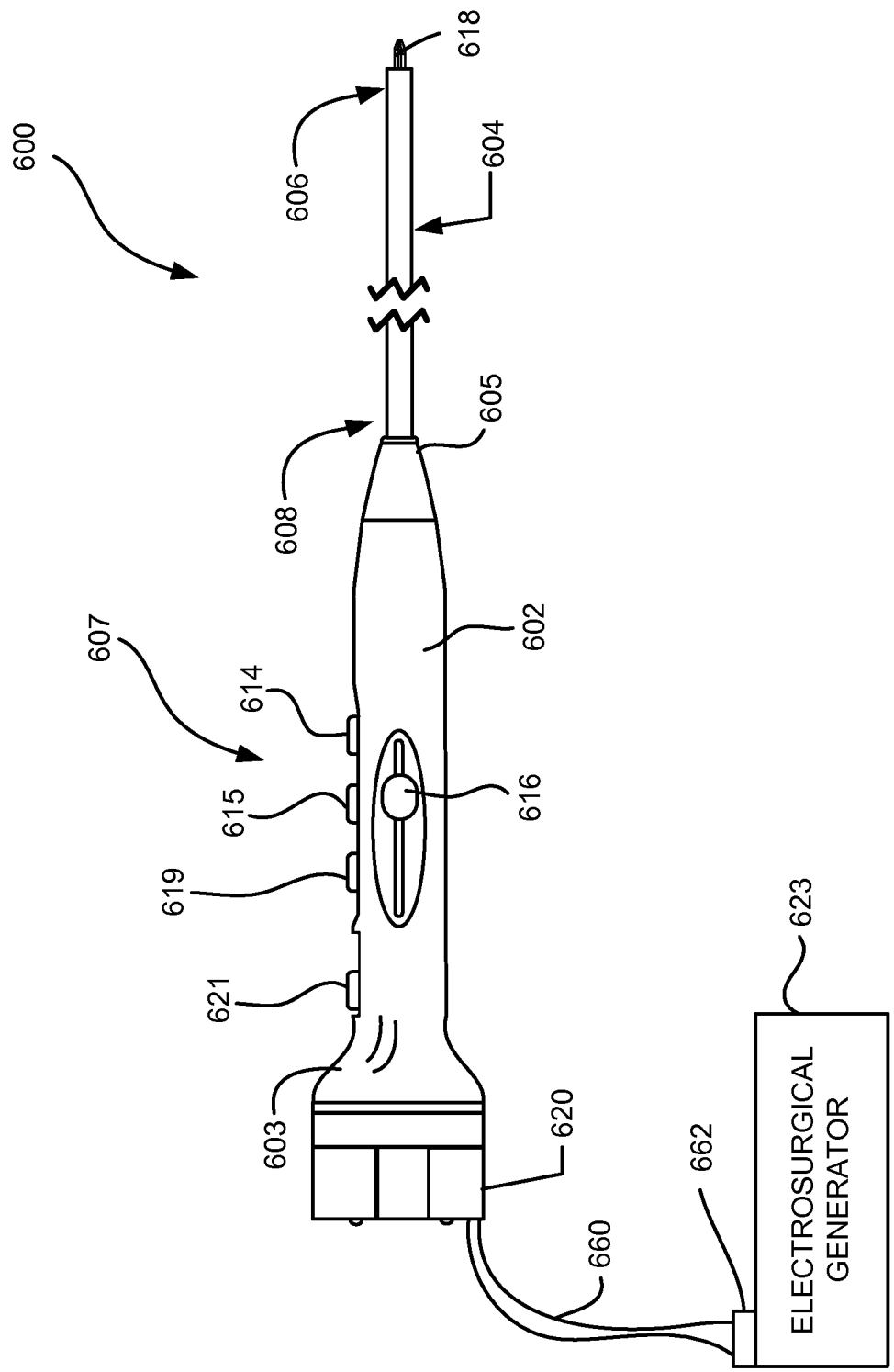
FIG. 9 is a side perspective view of an electrosurgical apparatus in accordance with another embodiment of the present disclosure.
Figure 10:
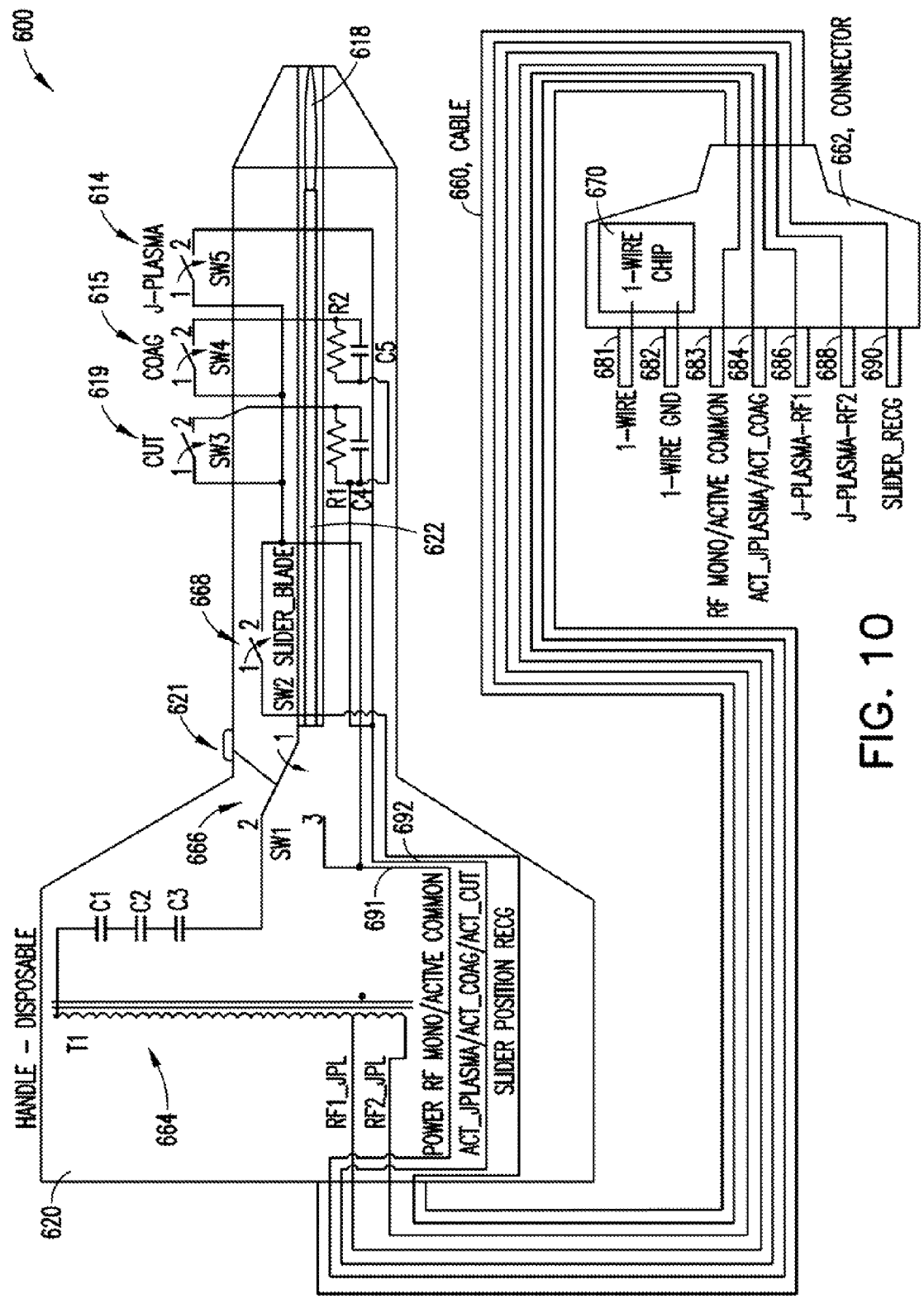
FIG. 10 is an electrical schematic diagram of the electrosurgical apparatus shown in FIGS. 9.
Figure 11:
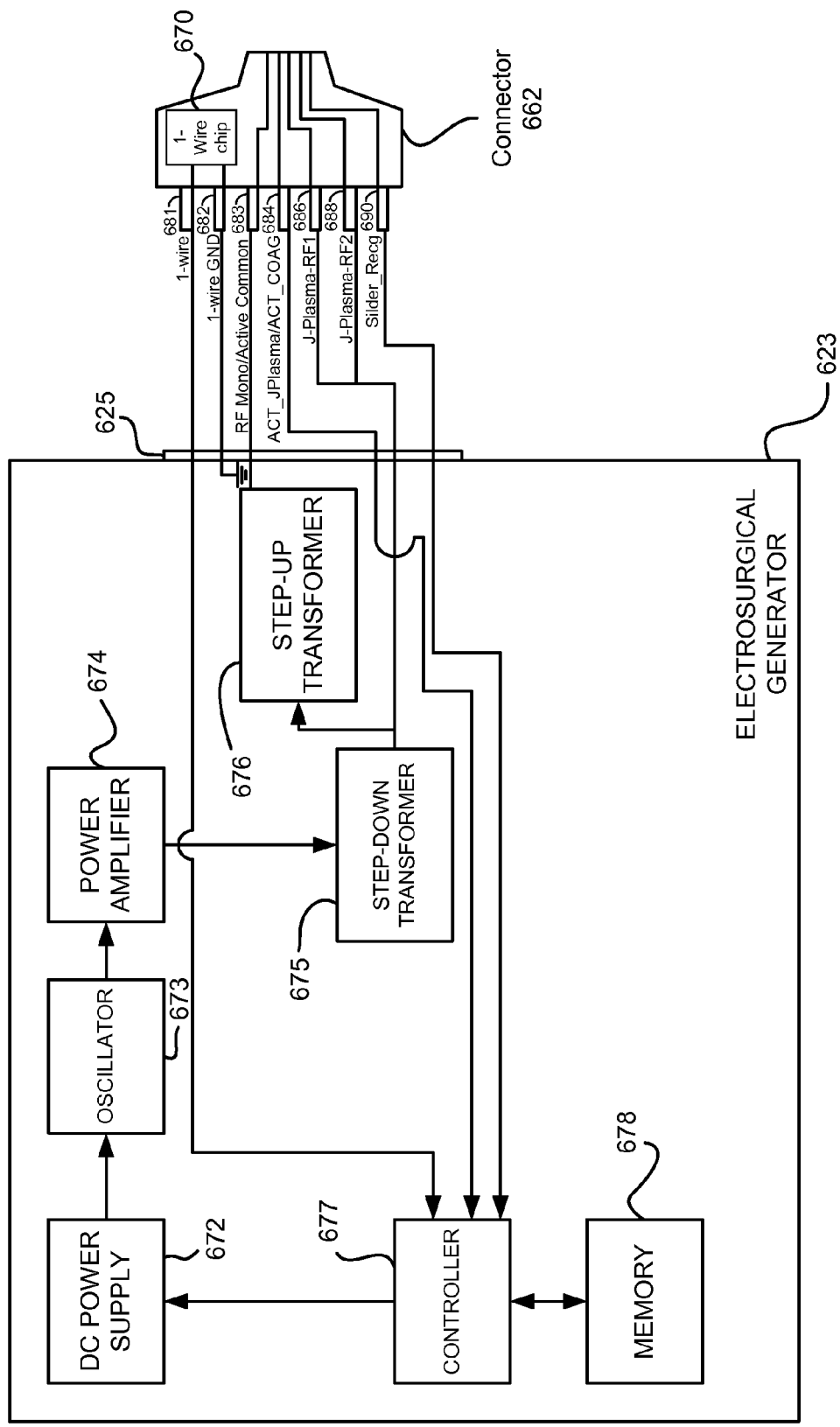
FIG. 11 is an electrical schematic diagram of an electrosurgical generator in accordance with an embodiment of the present disclosure.

Referring to FIGS. 9-11, an electrosurgical apparatus 600 in accordance with another embodiment of the present disclosure is illustrated. Generally, the apparatus 600 includes a housing 602 having a proximal end 603 and a distal end 605 and a tube 604 having an open distal end 606 and a proximal end 608 coupled to the distal end 605 of the housing 602, thereby forming a handpiece. The housing 602 includes a plurality of buttons 607, e.g., buttons 614, 615 and 619, and a first slider 616 and second slider 621. Activation of the first slider 616 will expose a blade 618 at the open distal end 606 of the tube 604, as described above. Activation of the second slider 621 sets the apparatus into different modes, as will be described below. Activation of the individual buttons 614, 615, 619 will apply electrosurgical energy to the blade 618 to affect different electrosurgical modes and, in certain embodiments, enable gas flow through an internal flow tube 622, as will be described in detail below. Additionally, a transformer assembly 620 is provided on the proximal end 603 of the housing 602 for coupling a source of radio frequency (RF) energy to the apparatus 600 via cable 660 and connector 662. The cable 660 includes a plurality of conductors for providing electrosurgical energy to the apparatus 600 and for communication signals to and from the apparatus 600 and an RF source, e.g., an electrosurgical generator 623. The connector 662 includes various pins, e.g., pins 681, 682, 683, 684, 686, 688 and 690, for coupling the connector 662 to corresponding port 625 on the generator 623, the details of which will be described below.

As can be seen in FIG. 11, the electrosurgical generator 623 includes a DC power supply 672, an oscillator 673, a power amplifier 674, a step-down transformer 675 and a step-up transformer 676 for supplying power to the apparatus 600. The electrosurgical generator 623 further includes a controller 677 and memory 678.

Referring back to FIG. 10, the transformer assembly 620 includes transformer T1 664, e.g., a step-up transformer, and at least one switch 666, which is controlled by the second slider 621. The switch 666 is coupled on one end to the conductive flow tube 622 and the other end of the switch 666 is adjustable between an output of transformer 664 and an output received directly from the generator 623 via pin 683, e.g., signal POWER_RF_MONO/ACTIVE_COMMON. The switch 666 is controlled by the second slider 621 located on the external surface of the housing 602. The second slider 621 may include a mechanism to lock the slider 621 in a particular position. In one embodiment, the second slider 621 controls the switch 666 and is interlocked to disable other buttons and/or sends signals to the generator 623 for selecting a mode. In another embodiment, the switch 666 may be coupled to the first slider 616 to select a mode based on the position of the conductive flow tube 622 and/or blade 618.

In a first position, switch 666 is coupled between terminal 2 and terminal 1 wherein an output of the transformer 664 is coupled to the conductive flow tube 622. In a second position, switch 666 is coupled between terminal 3 and terminal 1 wherein an output of the generator 623, i.e., an external source, is coupled to the conductive flow tube 622.

It is to be appreciated that switch 666 is to have very low stray capacitance between terminals 1 and 2 and terminals 1 and 3 to avoid mutual coupling of the transformer 664 and the lines from the generator. Step-up transformers 664 and 676 are both operated from the output of step-down transformer 675, so their outputs can be configured as to be in-phase. As a result, the potential difference between switch 666 contacts 2 and 3 can be small, depending on the load placed on either of those transformers. This will minimize potential arc-over between those contacts. Stray capacitance may, in general, be minimized by using a small contact area for contacts 2 and 3 of switch 666 (comparable to the area of the plates of a capacitor) within the limits of their current carrying requirements. Maximizing the distance between contacts 2 and 3 of switch 666 when it is in an open state will also reduce stray capacitance (comparable to the distance between two plates of a capacitor).

Furthermore, the position of the blade 618 determines the position of switch 668. Switch 668 is coupled to the connector 662 via a conductor, e.g., SLIDER_POSITION_RECG, which signals the generator as to the position of the blade 618 via pin 690. It is to be appreciated that switch 668 may be toggled between an open and closed position by being either directly or indirectly coupled to the slider 616 or the conductive flow tube 622.

Activation of the individual buttons 614, 615, 619 will apply electrosurgical energy to the blade 118 to affect different electrosurgical modes depending on the position of the blade 618. In the embodiment shown, button 614 is configured for activating the J-Plasma mode, button 615 is configured for activating a COAG (or coagulation) mode and button 619 is configured for activating a CUT mode. Two wires or conductors 691, 692 are used to recognize which of the buttons or switches 614, 615 or 619 are closed or activated. One of these wires, i.e., wire 691 coupled to pin 683, is also employed for applying RF power to blade 618 when switch 666 is coupled between terminal 3 and terminal 1 wherein an output of the generator 623 is coupled to the conductive flow tube 622. The other wire, i.e., wire 692 coupled to pin 684, is employed to allow controller 677 to sense which switch or button 614, 615 or 619 is activated. For example, when switch 614 is activated, the controller 677 senses 0 ohms; when switch 615 is activated, the controller 677 senses the parallel combination of resistor R2 and capacitor C5 at a given frequency; and when switch 619 is activated, the controller 677 senses the parallel combination of resistor R1 and capacitor C4 at a given frequency When the slider 616 retracts the blade 618 inside the opening of the tube 604, the J-Plasma mode is selected. In this mode, the J-Plasma button 614 is enabled while the COAG button 615 and CUT button 619 are mechanically and/or electrically disabled. Although not shown, the COAG button 615 and CUT button 619 may be mechanically disabled by a switch, relay, etc. In the J-Plasma mode, switch 666 is coupled between terminal 2 and terminal 1 wherein an output of the transformer 664 is coupled to the conductive flow tube 622. Additionally, switch 668 is closes, which signals the controller 677 in the generator 623 as to the position of the blade 618 and that the handpiece is in J-Plasma mode. Upon activation of button 614, a signal is sent to the generator 623 via pin 684, e.g., ACT_JPLASMA/

ACT_COAG/ACT_CUT, to initiate plasma generation. Subsequently, the generator supplies power via pin 686 along line RF1_JPL and via pin 688 along line RF2_JPL, via the step-down transformer 675 which provides power to step-up transformer 664. Furthermore, in J-Plasma mode, activation of button 614 initiates the flow of gas through the conductive flow tube 622. It is to be appreciated that in one embodiment the generator 623 coupled to the handpiece 600 may include an internal gas flow controller which receives the signal. In another embodiment, the gas flow controller is located externally of the generator 623 but may receive the gas activation signal from the generator. In a further embodiment, the gas flow controller is located externally of the generator 623 but may receive the gas activation signal from the handpiece itself via hardwired or wireless means.

When the slider 616 extends the blade 618 beyond the opening of the tube 604, the COAG/CUT mode is selected, also known as the general electrosurgery mode. In this mode, the COAG button 615 and CUT button 619 are enabled while the J-Plasma button 614 is mechanically and/or electrically disabled. Although not shown, the J-Plasma button 614 may be mechanically disabled by a switch, relay, etc. In the COAG/CUT mode, switch 666 is coupled between terminal 3 and terminal 1 wherein an output of the step-up transformer 676 in the generator 623 is coupled to the conductive flow tube 622, i.e., the transformer 664 is bypassed. Upon activation of buttons 615 or 619, a signal is sent to the generator via line ACT_JPLASMA/ACT_COAG/ACT_CUT to initiate supply of electrosurgical energy. Subsequently, the generator supplies power via pin 683 along line POWER_RF MONO/ACTIVE COMMON, which provides power to the conductive flow tube 622.

It is to be appreciated that the two step-up transformers 664, 676 (i.e., transformer 664 in the handpiece 600 for the J-Plasma mode and transformer 676 in the generator 623 for the general electrosurgery mode) have two different power curves. That is their output impedances are matched for different loading conditions. The J-Plasma transformer 664 in the handpiece 600 will put out higher voltages than the electrosurgery transformer 676 in the generator 623, but the J-Plasma transformer 664 is also matched for a higher output impedance for the combined tissue load and the plasma beam impedances in series. The electrosurgery transformer 676 back in the generator 623 has a lower output voltage, but higher current capability and its output impedance is matched to the lower impedance value of an electrosurgical blade 618 in direct contact with tissue. Exemplary values for the output in J-Plasma mode are 10 kilo ohm output impedance, 4 kV to 6 kV peak-to-peak and 140 mA, where the exemplary values for the output in electrosurgery mode are 150-250 ohm output impedance, 300 V to 6.5 kV peak-to-peak and 1.5 Amps. It is to be appreciated these exemplary values are for illustrative purposes only and in use the values may vary.

In some embodiments, gas may be provided to the handpiece 600 when in COAG/CUT mode. In one embodiment with the blade 618 extended, a mode button may be provided on the generator to enable gas to flow, e.g., CUT with gas. In another embodiment, when the blade 618 is retracted, fulguration or fulguration with gas may be enabled from a button in the generator.

In one embodiment, the connector 662 includes a one-wire chip 670, e.g., a memory, including information associated with the handpiece so the generator may recognize the handpiece. When coupled to a generator via pins 681 and 682, the controller 677 of generator 623 reads the information contained on the chip 670 and may perform or execute instructions based on the handpiece type. In other embodiment, the chip 670 may have read/write capabilities where the chip 670 can store how many times the handpiece has been used and provide that information to the generator. In certain embodiments, the controller 677 of generator 623 may store the number of uses of the apparatus 600 in memory 678 and determine that the handpiece 600 may no longer be used based on a predetermined use limit. In a further embodiment, the chip 670 may store application specific information for the handpiece that is to be loaded into the generator, e.g., a specific power profile of the handpiece. In another embodiment, the chip 670 may store information relating to the gas type to be used with the handpiece, e.g., Argon, Helium, etc. In this embodiment, the generator may provide an indication (or prevent operation) if the gas supplied does not match the type designated for the handpiece.

It is to be appreciated that the various features shown and described are interchangeable, that is, a feature shown in one embodiment may be incorporated into another embodiment.

While the disclosure has been shown and described with reference to certain preferred embodiments thereof, it will be understood by those skilled in the art that various changes in form and detail may be made therein without departing from the spirit and scope of the disclosure as defined by the appended claims.

Furthermore, although the foregoing text sets forth a detailed description of numerous embodiments, it should be understood that the legal scope of the invention is defined by the words of the claims set forth at the end of this patent. The detailed description is to be construed as exemplary only and does not describe every possible embodiment, as describing every possible embodiment would be impractical, if not impossible. One could implement numerous alternate embodiments, using either current technology or technology developed after the filing date of this patent, which would still fall within the scope of the claims.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. §112, sixth paragraph.

What is claimed is:
1. An electrosurgical apparatus comprising:
   a housing having a passage extending therethrough, the housing having a proximal end and a distal end;
   a flow tube having a proximal end and a distal end, the flow tube being disposed in the passage of the housing;
   an insulating outer tube having a proximal end and a distal end, the outer tube disposed around the flow tube with the proximal end of the outer tube coupled to the distal end of the housing, the flow tube being movable along a longitudinal axis of the housing and outer tube;
an electrode coupled to the distal end of the flow tube, and
a transformer assembly disposed on the proximal end of the housing, the transformer assembly including a first transformer configured to receive electrosurgical energy at a first predetermined value from an electrosurgical generator and an external input configured to receive electrosurgical energy at a second predetermined value from the electrosurgical generator, the transformer assembly further including a first switch for selectively coupling at least one of the first transformer and the external input to the electrode for providing electrosurgical energy thereto.

2. The electrosurgical apparatus of claim 1, further comprising a first slider member coupled to the flow tube for moving the flow tube thereby extending and retracting the electrode about the distal end of the outer tube, the first slider member being accessible on the housing.

3. The electrosurgical apparatus of claim 2, further comprising a second slider member coupled to the switch and configured to operate the switch, the second slider member being accessible on the housing.

4. The electrosurgical apparatus of claim 3, wherein the first transformer is a step-up transformer.

5. The electrosurgical apparatus of claim 4, wherein the external input is coupled to an external second transformer configured to provide the electrosurgical energy to the electrode at the second predetermined value.

6. The electrosurgical apparatus of claim 3, further comprising a plurality of buttons configured to affect at least one electrosurgical mode based on a position of the first switch.

7. The electrosurgical apparatus of claim 6, further comprising a connector having at least two pins configured to couple the apparatus to the electrosurgical generator.

8. The electrosurgical apparatus of claim 7, wherein the plurality of buttons include at least three buttons and are coupled to the connector via two conductors.

9. The electrosurgical apparatus of claim 7, wherein the connector includes a memory configured to store parameters of the at least one electrosurgical mode.

10. The electrosurgical apparatus of claim 3, further comprising a second switch configured to determine a position of the electrode and generate a signal indicating the position, the signal being transmitted to the electrosurgical generator.

11. The electrosurgical apparatus of claim 3, wherein the proximal end of the flow tube includes a connector for coupling to a gas source to enable gas to flow through the flow tube over the electrode.

12. The electrosurgical apparatus of claim 11, wherein when the electrode is retracted within the outer tube and is energized, plasma is formed when an inert gas flows through the electrically conducting tube.

13. An electrosurgical apparatus comprising:
an electrosurgical generator coupled to an electrical power supply configured to generate electrosurgical energy, the electrosurgical generator including a step-down transformer coupled to the electrical power source and a first step-up transformer coupled to an output of the step-down transformer; and
a handpiece including:
  a housing having a passage extending therethrough, the housing having a proximal end and a distal end;
  a flow tube having a proximal end and a distal end, the flow tube being disposed in the passage of the housing;
  an insulating outer tube having a proximal end and a distal end, the outer tube disposed around the flow tube with the proximal end of the outer tube coupled to the distal end of the housing, the flow tube being movable along a longitudinal axis of the housing and outer tube;
  an electrode coupled to the distal end of the flow tube, and
  a transformer assembly disposed on the proximal end of the housing, the transformer assembly including a second step-up transformer coupled to an output of the step-down transformer and a first switch for selectively coupling at least one of the first step-up transformer and the second step-up transformer to the electrode for providing electrosurgical energy thereto.

14. The electrosurgical apparatus of claim 13, wherein the housing further comprises a first slider member coupled to the flow tube for moving the flow tube thereby extending and retracting the electrode about the distal end of the outer tube, the first slider member being accessible on the housing.

15. The electrosurgical apparatus of claim 14, wherein the housing further comprises a second slider member coupled to the switch and configured to operate the switch, the second slider member being accessible on the housing.

16. The electrosurgical apparatus of claim 15, wherein the first step-up transformer is configured to provide electrosurgical energy to the electrode at a first predetermined value.

17. The electrosurgical apparatus of claim 16, wherein the second step-up transformer is configured to provide electrosurgical energy to the electrode at a second predetermined value.

18. The electrosurgical apparatus of claim 15, wherein the housing further comprises a plurality of buttons configured to affect at least one electrosurgical mode based on a position of the first switch.

19. The electrosurgical apparatus of claim 18, further comprising a connector having at least two pins configured to couple the handpiece to an electrosurgical generator via a cable having at least two conductors.

20. The electrosurgical apparatus of claim 19, wherein the plurality of buttons include at least three buttons and are coupled to the connector via two conductors.

21. The electrosurgical apparatus of claim 19, wherein the connector includes a memory configured to store parameters of the at least one electrosurgical mode.

22. The electrosurgical apparatus of claim 15, wherein the handpiece further comprises a second switch configured to determine a position of the electrode and generate a signal indicating the position, the signal being transmitted to a controller disposed in the electrosurgical generator.

23. An electrosurgical apparatus comprising:
a housing having a passage extending therethrough, the housing having a proximal end and a distal end;
a flow tube having a proximal end and a distal end, the flow tube being disposed in the passage of the housing;
an insulating outer tube having a proximal end and a distal end, the outer tube disposed around the flow tube with the proximal end of the outer tube coupled to the distal end of the housing, the flow tube being movable along a longitudinal axis of the housing and outer tube;
an electrode coupled to the distal end of the flow tube, and
an transformer assembly disposed on the proximal end of the housing, the transformer assembly including a first transformer configured to receive electrosurgical energy at a first predetermined value from an electrosurgical generator and an external input configured to receive electrosurgical energy at a second predetermined value from the electrosurgical generator, the transformer assembly further including a first switch for selectively coupling at least one of the first transformer and the first external input to the electrode for providing electrosurgical energy thereto, wherein the first transformer outputs electrosurgical energy to the electrode having a higher voltage than the electrosurgical energy of the external input.

24. An electrosurgical apparatus comprising:

a step-down transformer coupled to an electrical power source;

a first step-up transformer coupled to an output of the step-down transformer and configured to generate electrosurgical energy at a first predetermined value;

a second step-up transformer coupled to an output of the step-down transformer and configured to generate electrosurgical energy at a second predetermined value and a handpiece including:

a housing having a passage extending therethrough, the housing having a proximal end and a distal end;

a flow tube having a proximal end and a distal end, the flow tube being disposed in the passage of the housing;

an insulating outer tube having a proximal end and a distal end, the outer tube disposed around the flow tube with the proximal end of the outer tube coupled to the distal end of the housing, the flow tube being movable along a longitudinal axis of the housing and outer tube;

an electrode coupled to the distal end of the flow tube, and a first switch for selectively coupling at least one of the first step-up transformer and the second step-up transformer to the electrode for providing electrosurgical energy thereto.

\* \* \* \* \*